United States Patent [19]

Skolnick et al.

[11] Patent Number: 5,428,069

[45] Date of Patent: Jun. 27, 1995

[54] TREATING COGNITION WITH, AMINOCYCLOPROPANECARBOXYLIC DERIVATIVES

[75] Inventors: Phil Skolnick, Potomac, Md.; Ramon Trullas, Barcelona; Claudia P. Faiman, Barcelona; Eugenia Viu, Barcelona, all of Spain

[73] Assignee: The United States of America as represented by the Department of Health & Human Services, Washington, D.C.

[21] Appl. No.: 3,225

[22] Filed: Jan. 11, 1993

[51] Int. Cl.$^6$ .................... A61K 31/215; A61K 31/19
[52] U.S. Cl. ...................................... 514/531; 514/557
[58] Field of Search ............................... 514/531, 557

[56] References Cited

U.S. PATENT DOCUMENTS

| | | | |
|---|---|---|---|
| 4,570,014 | 2/1986 | Schroder et al. | 560/124 |
| 4,781,927 | 11/1988 | Zanno et al. | 426/3 |
| 4,788,332 | 11/1988 | Zanno et al. | 562/498 |
| 4,822,653 | 4/1989 | Zanno et al. | 423/3 |
| 5,086,072 | 2/1992 | Trullas et al. | 514/531 |

FOREIGN PATENT DOCUMENTS

WO89/05144  6/1989  WIPO.
WO91/01729  2/1991  WIPO.
WO91/19493 12/1991  WIPO.

OTHER PUBLICATIONS

Jones, et al., "Effects of NMDA Modulation in Scopolamine Dementia," 1991, *Annals of the New York Academy of Sciences*, 640:241–244.
Watson, et al., "Pharmacological Characteristics of Cyclic Homologues of Glycine at the N-Methyl-D-Aspartate Receptor-Associated Glycine Site," 1990, *Neuropharmacology*, 29(8):727–730.
J. Lehmann, "The NMDA Receptor," 1989, *Drugs of the Future*, 14(11):1060–1071.
T. W. Stone, "Excitatory Amino Acids," 1992, *Current Opinion in Therapeutic Patents*, 2(6):907–930.
Rao, et al., "Neuropharmacological Characterization of 1-aminocyclopropane-1-carboxylate and 1-aminocyclobutane-1-carboxylate, Ligands of the N-Methyl-D-Aspartate-Associated Glycine Receptor," 1990, *Neuropharmacology*, 29(3):305–309.
Wood, et al., "A Glycine Antagonist 7-Chlorokynurenic Acid Attenuates Ischemia-Induced Learning Deficits," 1993, *Neuroreport*, 4(2):151–154.
Smith, et al., "An NMDA Receptor-Associated Glycine Site Antagonist Attenuates Memory Loss After Experimental Brain Injury," 1990, *Soc. Neurosci. Abstr.*, 16(1):779.
Wood, et al., "7-Chlorokynurenic Acid Reduces CA1 Cell Loss in a Rate Model of Cerebral Ischemia in Vivo," 1991, *Soc. Neurosci. Abstr.*, 17:1265.
Zola-Morgan, et al., "Enduring Memory Impairment in Monkeys After Ischemic Damage to the Hippocampus," 1992, *The Journal of Neuroscience*, 12(7):2582–2596.
Watanabe, et al., "Involvement of Glycine Site Associated with the NMDA Receptor in Hippocampal Long-Term Potentiation and Acquisition of Spatial Memory in Rats," 1992, *Brain Research*, 582:58–64.

(List continued on next page.)

Primary Examiner—Marianne M. Cintins
Assistant Examiner—T. J. Criares
Attorney, Agent, or Firm—Townsend and Townsend Khourie and Crew

[57] ABSTRACT

The use of a compound possessing functional antagonist properties at the NMDA receptor complex through a specific action at the associated strychnine-insensitive glycine site to improve cognition in normal humans and to treat cognitive deficits resulting from chronic neuronal degeneration, acute brain injury, hypoxia, or other neurological disorders is provided. The compounds possessing functional antagonist properties comprise 1-aminocyclopropanecarboxylic acid, and its pharmaceutically acceptable esters, salts, and acid addition salts or 7-chlorokynurenic acid, and its pharmaceutically acceptable esters, amides, salts, ethers, and acid addition salts.

2 Claims, 6 Drawing Sheets

OTHER PUBLICATIONS

Collingridge et al. (1983) J. Physiol. 334:33–46.
Artola et al. (1987) Nature 330:649–652.
Kleinschmidt et al. (1987) Science 238:355–358.
Foster et al. (1987) Nature 329:395–396.
Galli et al. (1988) Pharmacol. Res. Comm. 20:407–408.
Bristow et al. (1986) Eur. J. Pharmacol. 126:303–307.
Kemp et al. (1988) Proc. Natl. Acad. Sci. USA 85:6547–6550.
Robinson et al. (1987) FASEB J. 1:446–455.
Hartley et al. (1990) Eur. J. Neurosci. 2:291–295.
Foster et al. (1990) Eur. J. Neurosci. 2:270–277.
Koek et al. (1990) J. Pharmacol. Exp. Ther. 252:349–357.
Skolnick et al. (1989) Life Sci. 45:1647–1655.
Evoniuk et al. (1991) Psychopharm. 105:125–128.
von Lubitz et al. (1992) Eur. J. Pharmacol., in press.
Boje et al. (1992) Brain Res. "Desensitization of the NMDA receptor complex by . . . granule cell cultures" (in press).
Patel et al. (1990) J. Neurochem. 54:849–854.
Ward et al. (1990) Pharm. Biochem. Behavior 35:785–790.
Staubli (1990) Psychobiology 18(3):267–268.
Staubli (1989) Behavioral Neurosci. 103:54–60.
Venable et al. (1990) Psychopharm. 100:215–221.
Sarter et al. (1992) Psychopharm. 107:461–473.
Upchurch et al. (1990) Psychopharm. 100:209–214.
Thompson et al. (1992) Nature 359:638–641.
Oliver et al. (1990) Int. J. Devl. Neurosci. 8(4):417–424.
Mondadori et al. (1992) Psychopharm. 108:11–15.
Chiamulera et al. (1990) Psychopharm. 102:551–552.
Baron et al. (1992) J. Pharmacol. Exp. Ther. 262:947–956.
Clissold et al. (1992) Behavioral Pharmacol. 3:393–402.
Trullas et al. (1991) Eur. J. Pharmacol. Elsevier, pp. 1–7.
Trullas et al. (1990) Eur. J. Pharmacol. Elsevier, pp. 1–10.
DeNoble et al. (1990) Eur. J. Pharmacol. Elsevier, pp. 197–202.
Danysz et al. (1989) Neurosci. Res. Comm. 5(1):9–18.
Mondadori et al. (1989) Exp. Brain Res. 75:449–456.
Wroblewski et al. (1989) Ann. Rev. Pharm. 29:441–474.
Collingridge et al. (1987) Trends Neurosci. 10:228–233.

TREATING COGNITION WITH AMINOCYCLOPROPANECARBOXYLIC DERIVATIVES

BACKGROUND OF THE INVENTION

1. Field of the Invention

This invention relates to the field of neuropsychiatry and relates specifically to methods for memory enhancement and treatment of memory deficits consequent to neurological disorders.

2. Description of the Background Art

The N-methyl-D-aspartate (NMDA) receptor, a subtype of excitatory amino acid receptor, has been suggested to mediate learning and memory processes. Intact hippocampal structure, which has a very high density of NMDA receptors, is necessary for the brain to process information and store it in memory. Electrophysiological studies have shown that NMDA receptors are required for the induction of long-term potentiation (LTP) in the hippocampus, a phenomenon that has been proposed to underlie storage of information in the brain and to mediate certain types of memory processes. However, a causal relationship between LTP and learning and memory processes has not been unequivocally demonstrated in mammals. The NMDA receptor also has been shown to be critically involved in various types of synaptic plasticity including enhanced synaptic transmission in the visual cortex; the kindling model of epilepsy; and vestibular compensation after unilateral labyrinthectomy.

The NMDA-sensitive glutamate receptor domain includes recognition sites (1) for the primary transmitter, with which agonists (e.g., NMDA and L-glutamate) and competitive antagonists (e.g., AP5 and PCP) interact; (2) a site through which glycine and drugs acting at the strychnine-insensitive glycine receptors bidirectionally modulate ion channel function; (3) a cation-binding site inside the channel; and (4) an inhibitory phencyclidine (PCP) site located within the receptor-operated cation channel.

The function of the NMDA receptor complex can be inhibited by drugs acting through several distinct mechanisms at the various recognition sites on the ligand-gated ion channel. For example, neurophysiological studies have demonstrated that glycine potentiates the response to activation of NMDA receptors in cultured brain neurons. This is a strychnine-insensitive action and it is postulated to result from activation of a supraspinal glycine receptor which modulates the opening of the Na+- Ca++ channel triggered by NMDA activation. The structural requirements for ligand binding to the strychnine-insensitive glycine receptors and their regional distribution in the central nervous system, with a high density in the hippocampus, have been reported to differ remarkably from strychnine-sensitive glycine receptors.

Glycine agonists are believed to facilitate NMDA transmission and to have a positive effect on cognition in certain types of learning. For example, D-cycloserine, which exhibits a good affinity for the strychnine-insensitive glycine receptor, has been shown to facilitate acquisition of a hippocampal associated learning task and has been suggested to improve cognition.

Competitive NMDA antagonists and channel blockers, like PCP and MK-801, also can affect certain types of memory and learning. For example, PCP and the use-dependent channel blocker MK-801 have been shown to interfere with the ability of mice and rats to perform in a passive avoidance test. However, other workers have demonstrated that PCP does not have a reliable effect on place learning.

To date, however, conventional methods and therapeutic agents have not proved to be effective or reliable for the improvement of cognition. For these reasons it would be desirable to provide improved methods which avoid the disadvantages of these conventional agents and methods while providing effective and reliable results.

SUMMARY OF THE INVENTION

The present invention provides methods for the improvement of cognitive function. More particularly, a method is provided wherein a patient receives, or is administered, a memory enhancing therapeutically effective dose or amount of a compound which possesses functional antagonist properties at the NMDA receptor complex through a specific action at the associated strychnine-insensitive glycine site.

Preferably, the functional antagonist comprises a compound having the formula:

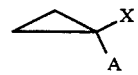

where A is -$CO_2H$, or a pharmaceutically acceptable ester, amide, or salt thereof, and X is -$NR^1R^2$ or a pharmaceutically acceptable acid addition salt thereof, where $R^1$ and $R^2$ are independently selected from the group consisting of hydrogen and lower alkyl, optionally which can be substituted with halogen, hydroxyl, alkoxy, oxo, mercapto, aryl, or amino, or $R^1$ and $R^2$ together with the nitrogen to which they are attached form a substituted 5-membered or 6-membered heterocycle which also can contain another heteroatom such as oxygen, sulfur, or nitrogen. In a preferred embodiment, the functional antagonist comprises 1-aminocyclopropanecarboxylic acid, or a pharmaceutically acceptable ester, amide, or salt thereof.

In another aspect of this invention, the functional antagonist comprises a compound having the formula:

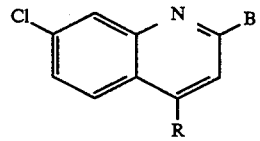

where B is -$CO_2H$, or a pharmaceutically acceptable ester, amide, or salt thereof, and R is -OH, or a pharmaceutically acceptable ester, ether, or salt thereof, or its pharmaceutically acceptable acid addition salts. In a preferred embodiment, the functional antagonist comprises 7-chlorokynurenic acid, or a pharmaceutically acceptable ester, amide, salt, ether, or acid addition salt thereof.

This invention also provides a method to treat a cognitive deficit consequent to a neurological disorder, whereby a therapeutically-effective amount of a compound which possesses functional antagonist properties at the NMDA receptor complex through a specific action at the associated strychnine-insensitive glycine site is administered to a patient.

The neurological disorder typically is the result of chronic neuronal degeneration or acute brain injury. More specifically, the following neurological disorders are included within the definition: epilepsy (or seizures); hypoxia, either alone (e.g., carbon monoxide poisoning, near drowning) or combined with ischemic blood flow reduction (e.g., cardiac arrest, stroke); anxiety; affective disorders; memory dysfunction linked to the aging process; and neurodegenerative diseases (e.g., Guam anti-lymphocyte serum (ALS), Parkinson disease, dementia and lathyrism). The methods of the present invention can also be employed in the treatment of memory impairment following acute brain injury, such as head trauma or multi-infarct dementia.

DETAILED DESCRIPTION OF THE INVENTION

1. Definitions and General Parameters

Figure 1:
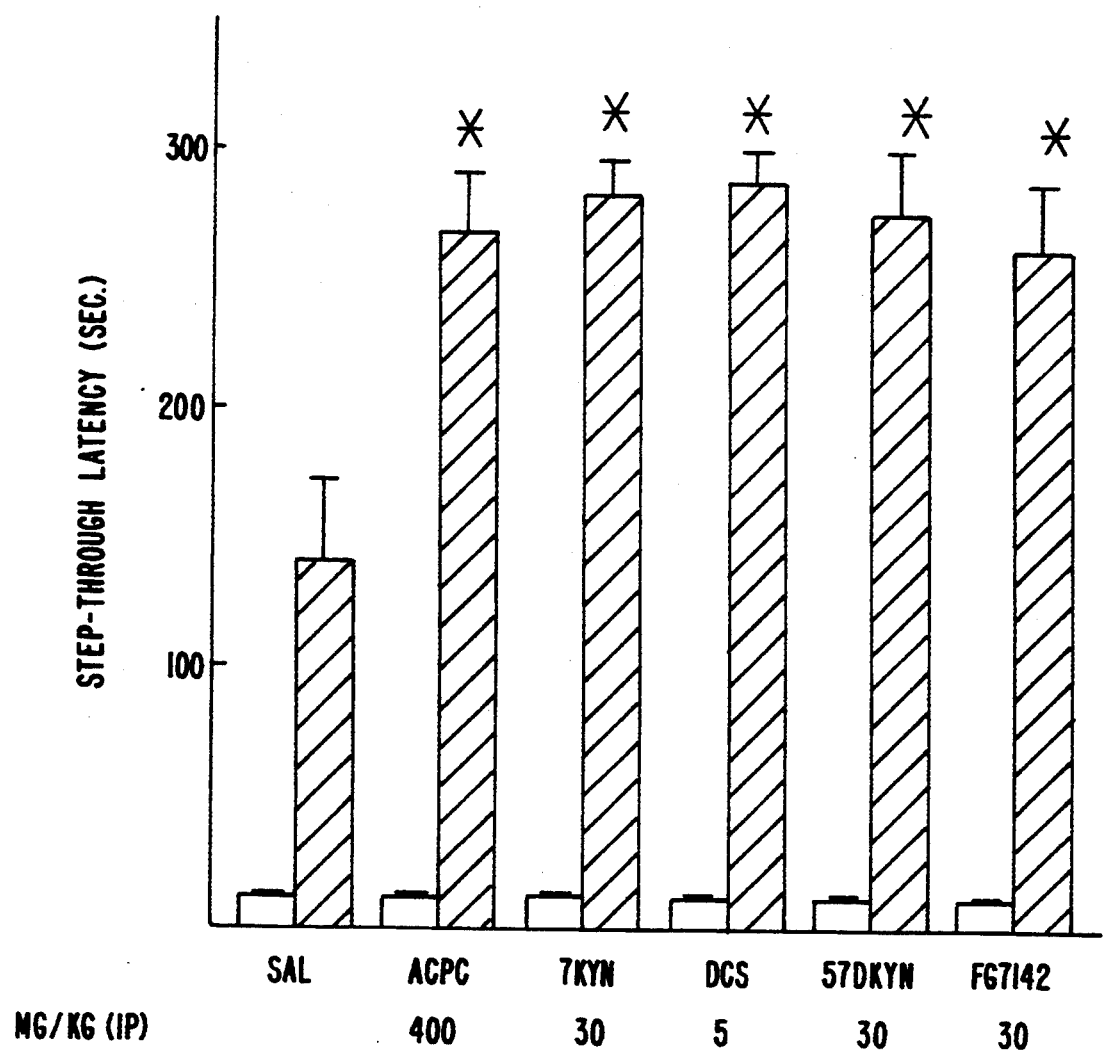
FIG. 1 is a graphical representation depicting the effects of glycinergic compounds and N-methyl-$\beta$-carboline-3carboxamide (FG7142) on passive avoidance acquisition-retention 24 hours after training. All compounds were administered intraperitoneal (i.p.) 30 minutes before training. Training was performed with a 0.25 milliampere (mA) shock. Testing was 24 hours after training. Unfilled bars represent latency of non-shocked animals. Hatched bars represent latency 24 hours after training. The symbol "*" represents results that were significantly different from the saline group ($p<0.05$ Mann-Whitney U-test). (See, e.g., Goldstein, "Biostatistics: An Introductory Text", The MacMillan Co., New York, pp. 55–59 (1968)). These data demonstrate that functional NMDA receptor antagonists at the strychnine-insensitive glycine site facilitate learning and memory of an inhibitory avoidance task (i.e., a passive avoidance task). The facilitatory effect observed with these compounds was similar to that observed with D-cycloserine, a positive NMDA modulator at the strychnine-insensitive glycine site, and with FG7142, a benzodiazepine receptor inverse agonist.

Unless otherwise stated, the following terms used in the specification and claims have the meanings given below:

"Improvement of cognitive function" embraces treatment to improve or enhance memory and/or treatment to address a cognitive deficit consequent to a neurological disorder.

"Neurological disorder" as utilized herein, unless otherwise qualified, means a disorder resulting from acute brain injury or chronic neuronal degeneration. More specifically, the following neurological disorders are included within the definition: epilepsy (or seizures); hypoxia, either alone (e.g., carbon monoxide poisoning, near drowning) or combined with ischemic blood flow reduction (e.g., cardiac arrest, stroke); anxiety; affective disorders; and neurodegenerative diseases (e.g., Guam ALS, Parkinson disease, dementia and lathyrism).

"Functional antagonist at the strychnine-insensitive glycine receptor" refers to a compound that binds to the strychnine-insensitive glycine site of the NMDA receptor and has the functional consequence of reducing or antagonizing the effects of glutamate or NMDA effected through the NMDA receptor, as exemplified in, for example, a neurotoxicity assay (see Boje et al. (1992) *Brain Research*, "Desensitization of the NMDA receptor complex by glycinergic ligands in cerebellar granule cell cultures" (in press), portions of which are reproduced below, and Patel et al. (1990) *J. Neurochem.* 54:849–854). According to the present invention, functional antagonists at the strychnine-insensitive glycine receptor refers to those compounds possessing functional antagonist properties at the NMDA receptor complex through a specific action at the associated strychnine-insensitive glycine site.

"Competitive antagonist" refers to an antagonist that combines reversibly with the same binding sites of the receptor as the active drug and can be displaced from these sites by an excess of an agonist or antagonist with a greater binding affinity for the binding sites.

"Noncompetitive antagonist" refers to a substance that interacts at a distinct binding site and blocks the approach of an agonist to its binding site. Since they bind at distinct loci, noncompetitive antagonists are not displaced with increasing concentrations of agonist.

According to the present invention, "inhibitory avoidance task" and "passive avoidance task" are equivalent and intended to refer to paradigms involving learning in response to aversive stimuli.

"Pharmaceutically acceptable ester" refers to those esters which retain, upon hydrolysis of the ester bond, the biological effectiveness and properties of the carboxylic acid or alcohol and are not biologically or otherwise undesirable. For a description of pharmaceutically acceptable esters as prodrugs, see Bundgaard, H., ed., (1985) *Design of Prodrugs*, Elsevier Science Publishers, Amsterdam. These esters are typically formed from the corresponding carboxylic acid and an alcohol. Generally, ester formation can be accomplished via conventional synthetic techniques. (See, e.g., March *Advanced Organic Chemistry*, 3rd Ed., John Wiley & Sons, New York (1985) p. 1157 and references cited therein, and Mark et al. *Encyclopedia of Chemical Technology*, John Wiley & Sons, New York (1980).) The alcohol component of the ester will generally comprise (i) a $C_2$–$C_{22}$ aliphatic alcohol that can or can not contain one or more double bonds and can or can not contain branched carbon chains or (ii) a $C_7$–$C_{12}$ aromatic or heteroaromatic alcohols. This invention also contemplates the use of those compositions which are both esters as described herein and at the same time are the pharmaceutically acceptable acid addition salts thereof.

"Pharmaceutically acceptable amide" refers to those amides which retain, upon hydrolysis of the amide bond, the biological effectiveness and properties of the carboxylic acid or amine and are not biologically or otherwise undesirable. For a description of pharmaceutically acceptable amides as prodrugs, see Bundgaard, H., ed., (1985) *Design of Prodrugs*, Elsevier Science Publishers, Amsterdam. These amides are typically formed from the corresponding carboxylic acid and an amine. Generally, amide formation can be accomplished via conventional synthetic techniques. (See, e.g., March *Advanced Organic Chemistry*, 3rd Ed., John Wiley & Sons, New York (1985) p. 1152 and Mark et al. *Encyclopedia of Chemical Technology*, John Wiley & Sons, New York (1980).) This invention also contemplates the use of those compositions which are both amides as described herein and at the same time are the pharmaceutically acceptable acid addition salts thereof.

"Pharmaceutically acceptable ether" refers to those ethers which retain, upon hydrolysis of the ether bond, the biological effectiveness and properties of the hydroxyl containing compound and are not biologically or otherwise undesirable. For a description of pharmaceutically acceptable ethers as prodrugs, see Bundgaard, H., supra. Generally, ether formation can be accomplished via conventional synthetic techniques. (See, e.g., March *Advanced Organic Chemistry*, 3rd Ed., John Wiley & Sons, New York (1985) p. 1161.) According to the instant invention, ethers will typically be generated from 7-chlorokynurenic acid and a alkyl halide, an aryl halide, an arylalkyl halide, or a heteroaryl halide.

"Pharmaceutically acceptable salt" refers to those salts which retain the biological effectiveness and properties of the carboxylic acid and which are not biologically or otherwise undesirable, formed with alkali metal bases such as sodium or potassium; alkaline earth metal bases such as calcium; and with organic bases such as tromethamine, diethylamine, ethanolamine, piperidine, isopropylamine, choline, caffeine, and the like. For a description of pharmaceutically acceptable salts as prodrugs, see Bundgaard, H., supra.

"Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, menthanesulfonic acid, ethanesulfonic acid, p-toluenesulfonic acid, salicylic acid and the like. For a description of pharmaceutically acceptable acid addition salts as prodrugs, see Bundgaard, H., supra.

"Alkyl" refers to a cyclic, branched, or straight chain alkyl group containing only carbon and hydrogen. This term is further exemplified by groups such as methyl, heptyl, -$(CH_2)_2$-, and adamantyl. Alkyl groups can either be unsubstituted or substituted with one or more non-interfering substituents, e.g., halogen, alkoxy, acyloxy, hydroxy, mercapto, carboxy, benzyloxy, phenyl, benzyl, or other functionality which has been suitably blocked with a protecting group so as to render the functionality non-interfering. Each substituent can be optionally substituted with additional non-interfering substituents. The term "non-interfering" characterizes the substituents as not adversely affecting any reactions to be performed in accordance with the process of this invention.

"Lower alkyl" refers to an alkyl group having one to nine carbon atoms, which can be straight or branched, including, for example, methyl, ethyl, propyl, isopropyl, butyl, isobutyl, tertbutyl, amyl, hexyl, heptyl, octyl, nonyl, and the like.

"Halogen" refers to fluorine, chlorine, bromine, and iodine atoms.

"Hydroxyl" refers to -OH.

"Alkoxy" refers to the group alkyl-O-.

"Oxo" refers to the C=O or carbonyl group.

"Mercapto" refers to a -SH group.

"Amino" refers to -NH$_2$.

"Aryl" or "Ar" refers to a monovalent aromatic carbocyclic group having a single ring (e.g., phenyl) or multiple condensed rings (e.g., naphthyl or anthryl), which can optionally be unsubstituted or substituted with hydroxy, lower alkyl, alkoxy, chloro, halo, mercapto, and other non-interfering substituents.

"Heterocycle" refers to a monovalent saturated or aromatic carbocyclic group having a single ring (e.g., pyrrolidyl, pyridyl or furyl) or multiple condensed rings (e.g., indolizinyl or benzo[b]thienyl) and having at least one heteroatom, such as N, O or S, within the ring, which can optionally be unsubstituted or substituted with hydroxy, alkyl, alkoxy, halo, mercapto, and other non-interfering substituents.

"Arylalkyl" refers to the groups -R-Ar and -R-HetAr, where Ar is an aryl group, HetAr is a heteroaryl group, and R is straight-chain or branched-chain aliphatic group. Examples of arylalkyl groups include benzyl and furfuryl.

"Therapeutically- or pharmaceutically-effective amount" as applied to the compositions of the instant invention refers to the amount of composition sufficient to induce a desired biological result. That result can be alleviation of the signs, symptoms, or causes of a disease, or any other desired alteration of a biological system. In the present invention, the result will involve the improvement or enhancement of memory or the treatment of a cognitive deficit linked to a neurological disorder.

"Pharmaceutically or therapeutically acceptable carrier" refers to a carrier medium which does not interfere with the effectiveness of the biological activity of the active ingredients and which is not toxic to the host or patient.

The following list of abbreviations utilized herein is also provided to remove any vagueness which can exist to their meanings:

N-methyl-D-aspartate, NMDA;
1-aminocyclopropanecarboxylic acid, ACPC;
7-chlorokynurenic acid or 7-chloro-4-hydroxyquinoline- 2-carboxylic acid, 7KYN;
5,7-dichlorokynurenic acid, 5,7DKYN;
diazepam, DZP;
2-amino-7-phosphonoheptanoic acid, AP7;
glycine, GLY;
N-methyl-8-carboline-3-carboxamide, FG7142;
(+)-5-Methyl-10,11-dihydro-5H-dibenzo[a,d]cyclohepten-5,10-imine, MK-801;
pentylenetetrazol, PTZ;
D-cycloserine, DCS; and
saline, SAL.

2. Compounds

The present invention provides for the administration of compounds which possess functional antagonist properties at the NMDA receptor complex through a specific action at the associated strychnine-insensitive glycine site to a patient to improve cognitive function. Examples of functional antagonists include the competitive antagonist 7-chlorokynurenic acid (7KYN) and the partial agonist 1-aminocyclopropanecarboxylic acid (ACPC). These functional antagonists block many of the biochemical and pharmacological actions of excess stimulation of the NMDA receptor complex. For example, these compounds reduce the neurotoxic effects of NMDA and/or glutamate that are mediated through the NMDA receptor complex. 7KYN has also been shown to block LTP. In addition, these two substances do not appear to share many of the undesirable side effects common to competitive NMDA antagonists and channel blockers. Other functional antagonists can be identified through the procedure set forth in Boje et al. supra.

In one preferred embodiment of this invention, the compound which possesses functional antagonist properties at the NMDA receptor complex through a specific action at the associated strychnine-insensitive glycine site will comprise a compound having the formula:

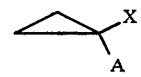

where A is -CO$_2$H, or a pharmaceutically acceptable ester, amide, or salt thereof, and X is -NR$^1$R$^2$ or a pharmaceutically acceptable acid addition salt thereof where R$^1$ and R$^2$ are independently selected from the group consisting of hydrogen and lower alkyl, optionally substituted with halogen, hydroxyl, alkoxy, oxo, mercapto, aryl, or amino, or R$^1$ and R$^2$ together with the nitrogen to which they are attached form a substituted 5-membered or 6-membered heterocycle which can also contain another heteroatom such as oxygen, sulfur, or nitrogen. In a preferred embodiment, the functional antagonist comprises 1-aminocyclopropanecarboxylic acid, and pharmaceutically acceptable esters, amides, and salts thereof. In a preferred embodiment, the functional antagonist comprises 1-aminocyclopropanecarboxylic acid.

These compounds can be commercially purchased or can generally be prepared by methods readily known and understood by those skilled in the art. For example, esters of ACPC can be prepared by Fischer esterification of the parent carboxylic acid. Additionally, for example, compounds wherein "X" is a lower alkylamino or lower dialkylamino moiety can be easily prepared by reacting ACPC with lower alkyl halides. In a preferred embodiment, the functional antagonist comprises 1-aminocyclopropanecarboxylic acid.

In a further preferred embodiment of this invention, the compound which possesses functional antagonistic properties at the NMDA receptor complex through a specific action at the associated strychnine-insensitive glycine site will comprise a compound having the formula:

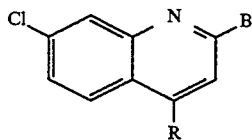

where B is -CO$_2$H, or a pharmaceutically acceptable ester, amide, or salt thereof, and R is -OH, or a pharmaceutically acceptable ester, ether or salt thereof, and its pharmaceutically acceptable acid addition salt thereof. These compounds can be commercially purchased or can generally be prepared by methods readily known and understood by those skilled in the art. In a preferred embodiment, the functional antagonist comprises 7-chlorokynurenic acid, and pharmaceutically acceptable esters, amides, salts, ethers, and acid addition salts thereof.

3. In Vivo Administration

In a further embodiment, a method to improve or enhance memory is described whereby a therapeutically-effective amount of a compound which possesses functional antagonist properties at the NMDA receptor complex through a specific action at the associated strychnine-insensitive glycine site is administered to a patient. The methods of the present invention also can be used to treat a cognitive deficit consequent to many memory-related neurological disorders, whereby a therapeutically-effective amount of a compound having functional antagonist properties at the NMDA receptor complex through a specific action at the associated strychnine-insensitive glycine site is administered to a patient. Such disorders can be the result of chronic neuronal degeneration or can be the result of acute brain injury. More specifically, the following neurological disorders are included within the definition: epilepsy (or seizures); hypoxia, either alone (e.g., carbon monoxide poisoning, near drowning) or combined with ischemic blood flow reduction (e.g., cardiac arrest, stroke); anxiety; affective disorders; memory dysfunction linked to the aging process; and neurodegenerative diseases (e.g., Guam ALS, Parkinson disease, dementia and lathyrism). The methods of the present invention can also be employed in the treatment of memory impairment following acute brain injury, such as head trauma or multi-infarct dementia.

While it is possible to administer the active ingredient of this invention alone, it is preferable to present it as part of a pharmaceutical formulation. The formulations of the present invention comprise at least one compound of this invention in a therapeutically- or pharmaceutically-effective dose together with one or more pharmaceutically or therapeutically acceptable carriers and optionally other therapeutic ingredients. Various considerations are described, e.g., in Gilman et al. (eds) (1990) *Goodman and Gilman's: The Pharmacological Bases of Therapeutics*, 8th Ed., Pergamon Press; and *Remington's Pharmaceutical Sciences*, Mack Publishing Co.: Easton, PA, 17th Ed. (1985). Methods for administration are discussed therein, e.g., for oral, intravenous, intraperitoneal, or intramuscular administration, and others. Pharmaceutically acceptable carriers will include water, saline, buffers, and other compounds described, e.g., in the Merck Index, Merck & Co., Rahway, N.J.

The pharmaceutical compositions will be administered by parenteral or oral administration for therapeutic treatment. The pharmaceutical compositions can be administered in a variety of unit dosage forms depending upon the method of administration. For example, unit dosage forms suitable for oral administration include powder, tablets, pills, capsules and dragees.

The pharmaceutical compositions will often be administered intravenously. Thus, this invention provides compositions for intravenous administration which comprise a solution of the compound dissolved or suspended in an acceptable carrier, preferably an aqueous carrier. A variety of aqueous carriers can be used, e.g., water, buffered water, 0.9% saline, and the like. These compositions will sometimes be sterilized by conventional, well known sterilization techniques, or can be sterile filtered. The resulting aqueous solutions can be packaged for use as is, or lyophilized, the lyophilized preparation being combined with a sterile aqueous solution prior to administration. The compositions can contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, and the like.

For solid compositions, conventional nontoxic solid carriers can be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 0.1–95% of active ingredient, preferably about 20%.

In therapeutic applications, compositions are administered to a patient in an amount sufficient to at least partially improve cognition or enhance memory. An amount adequate to accomplish this is defined as "therapeutically-effective amount or dose." Amounts effective for this use will depend on the improvement desired and the weight and general state of the patient.

Compounds will preferably be administered in a daily dose. The daily dose, of course, will vary with the nature of the active ingredient. For example, generally, ACPC will be administered in a range from about 100 mg to about 1000 mg per kilogram of body weight per day, whereas 7KYN will be administered in a range from about 1 mg to about 100 mg per kilogram of body weight per day. A more preferred dosage of ACPC will range from about 200 mg to about 800 mg per kilogram of body weight and most preferred is a dosage of about 400 mg per kilogram of body weight per day. A more preferred dosage of 7KYN will range from about 10 mg to about 50 mg per kilogram of body weight and most preferred is a dosage of about 30 mg per kilogram of body weight per day. The dosages for other functional antagonist will generally be in a range of about 0.1 mg to about 1000 mg per kilogram of body weight per day.

A suitable dose can be administered in multiple sub-doses per day. These sub-doses can be administered in unit dosage forms. Typically, a dose or sub-dose can contain from about 1 mg to about 500 mg of active compound per unit dosage form. A more preferred dosage will contain from about 10 mg to about 100 mg of active compound per unit dosage form.

In order that the invention described herein can be more fully understood, the following examples are set forth. It should be understood that these examples are for illustrative purposes only, and are not to be construed as limiting this invention in any manner.

EXPERIMENTAL

Neurotoxicity Assay

The following procedure can be employed to identify NMDA functional antagonists as described in Boje et al. supra.

Cerebellar Granule Cell Cultures

Primary cultures of cerebellar granule cells were prepared from 6-8 day old Sprague-Dawley rat pups using the method of Gallo et al. (1982) *Proc. Natl. Acad. Sci. USA* 79:7919-7923. Dissociated cells were plated on poly-L-lysine coated 35 millimiter (mm) plates at a density of $2.2-3.8 \times 10^5$ cells/square centimeter (cm$^2$). Cultures were grown in Eagle's Basal Media containing 10% fetal calf serum, 2 millimolar (mM) L-glutamine, 0.1 milligram/milliliter (mg/ml) gentamicin, and 25 mM potassium chloride (KCl). Others agents are added as indicated without a change in culture media. Cytosine arabinoside (10 micromolar ($\mu$M)) was added 18 to 24 hours after plating to inhibit the growth of non-neuronal cells. Cultures prepared by this method were >90% enriched in granule neurons.

Assay Procedure

Experiments were performed using cultures grown for eight days after plating. Conditioned media from naive cultures were reserved for later use. Cultures were washed twice with 1.5 ml aliquots of modified Locke's buffer without magnesium and glucose (154 mM sodium chloride (NaCl), 5.6 mM KCl, 2.3 mM calcium chloride ($Ca_2Cl_2$), 8.6 mM HEPES, pH 7.4). After a 25 minute preincubation in 1 ml Locke's buffer at 37° C., the cultures were preincubated for 15 minutes in 1 ml of fresh Locke's buffer containing glycinergic ligands where appropriate. The total preincubation time in modified Locke's buffer was 40 minutes, which was previously established as a sufficient period of time to render cultured cerebellar granule neurons susceptible to L-glutamate toxicity (see Lysko et al. (1989) *Brain Research* 499:258-266).

Neurotoxicity was induced by a thirty minute incubation with L-glutamately at 37° C. The cultures were washed twice with 1.5 ml aliquots of Hank's Balanced Salt Solution at the end of this incubation period. One ml of conditioned media was added to the cultures, and the cultures were returned to the incubator. In experiments examining the potential neuroprotective effects of prolonged exposure to glycinergic ligands, cultures were incubated for 20-24 hours with various agents (final concentration, 1000 $\mu$M) prior to the washing, preincubation, and glutamate neurotoxicity protocol.

Neuronal cell death was determined 18-24 hours after exposure to the indicated concentrations of glutamate. Viable and dead cells were quantitated by trypan blue staining in 3 random fields under 400X magnification. Neuronal cell death (expressed as % dead neurons) after various treatments was calculated after subtracting the % dead neurons in control cultures incubated with only modified Locke's buffer. This basal cell death was $25 \pm 1.5\%$ (X$\pm$SEM, n=29).

Compounds which possesses functional antagonist properties at the NMDA receptor complex through a specific action at the associated strychnine-insensitive glycine site will exhibit a neuroprotective effect in this assay. For example, ACPC (1000 $\mu$M) produced a statistically significant ($p<0.01$) but incomplete (50%) reduction in cell death, while 7KYN afforded essentially complete neuroprotection. DCS (1000 $\mu$M) had no neuroprotective effect.

Subjects

Experimentally naive male NIH-Swiss mice (Harlan Sprague-Dawley, Inc., Frederick, Md.) weighing 20-25 grams (g) were housed ten per cage ($25 \times 50 \times 15$ centimeters (cm)) with food and water freely available. They were kept in a regulated environment for at least one week before they were used, lights on from 0600 to 1800 hours at a room temperature of 22°-25° C. with a relative humidity of 50% $\pm$10%.

Apparatus and Procedure

Animals were trained on a step-through inhibitory avoidance apparatus located in a dark room next to the housing room. The apparatus was similar to that described by Weiskrantz and Mondadori (1991) *Psychopharmacology* 105:145-150 and by Baratti et al. (1984) *Behav. Neural Biol.* 40:155-169 with slight modifications. The apparatus consisted of a platform made of white lucite ($5 \times 5$ cm), illuminated with a 25 Watt (W) bulb positioned 15 cm directly above. The platform was located 11.5 cm high on the outside of one wall of a black plastic box ($12 \times 12 \times 30.5$ cm). A small triangular opening ($3.5 \times 3.5 \times 3.5$ cm) in the wall with a sliding door provided access from the platform to the dark interior of the box which contained a metallic grid floor at platform level and a removable lid (19 cm above the grid floor). The grid floor was connected to a scrambler shock generator (Letica, Barcelona, Spain). Each mouse was placed on the white lighted platform and the time spent to enter the dark compartment (step-through) latency was measured. When the mouse stepped into the dark compartment with its four paws, the hole was closed with the sliding door and a one second foot-shock was administered. Different foot-shock intensities (ranging from 0.25 to 0,625 mA) were used according to the experimental design. For retention tests, which took place at different periods after training, each mouse was placed on the lighted platform again and individual step-through latencies were recorded (cut off time 300 seconds).

To investigate the effects of functional NMDA antagonists on memory disruption induced by neuronal damage, animals were exposed to an hypoxic environment for 30 minutes immediately before inhibitory avoidance training. The hypoxia chambers were 400 ml glass beakers (12.5 cm$\times$7.5 cm) covered with a rubber stopper and continuously perfused with a gas mixture consisting of 7% oxygen and 93% nitrogen or other inert gases. The flow rate was adjusted such that the gas turnover in each chamber was one liter per minute. Oxygen concentration was continuously monitored in one of the hypoxia chambers with an oxygen sensor (Oxymetre Hospitalier, Bioblock Sci., Cedex, France).

Drugs

Mice were injected intraperitoneally (0.1-0.2 ml) with either vehicle or drugs. The following drugs were used: 1-aminocyclopropanecarboxylic acid (ACPC, Tocris Neuramin, Essex, UK); 7-chlorokynurenic acid (7KYN, Tocris Neuramin, Essex, UK); diazepam (DZP, Prodesfarma, Barcelona, Spain); pentylenetetrazol (PTZ, Sigma, St. Louis, Mo.); 2-amino 7-phosphonoheptanoic acid (AP7, Research Biochemical Inc., Natick, Mass.); (+) MK-801 hydrogen maleate (MK-801, Research Biochemical Inc., Natick, Mass.); glycine (GLY, Flyka Chemie, Buchs, Switzerland); 5,7-dichlorokynurenic acid (5,7DKYN, Tocris Neuramin, Essex, UK); and N-methyl-β-carboline-3-carboxamide (FG7142, Research Biochemical Inc., Natick, Mass.). ACPC, PTZ, DCS, MK-801, and GLY were dissolved in saline. AP7, 7KYN, and 5,7DKYN were dissolved in 1.0 normal (N) aqueous sodium hydroxide (5–8% of volume) and then saline added to volume. DZP and FG7142 were suspended in diluted Tween 80 (polyoxyethylene (20) sorbitan monooleate, Aldrich Chemical Company, Inc., Milwaukee, Wis.).

Statistics

Statistical analyses were performed using the Kruskal-Wallis one way Analysis of Variance (ANOVA) and Mann-Whitney U tests for comparisons between groups. Mean and standard error (SEM) were used for graphical representations. (See, e.g., Goldstein, "Biostatistics: An Introductory Text" The MacMillan Co., New York, pp. 55–59 (1968)).

Results

An animal model that is widely viewed to reflect memory processes in man and to have predictive ability in assessing memory enhancing or debilitating processes in humans was utilized to demonstrate memory enhancement. (See Mondadori et al. (1992) *Psychopharmacology* 108:11–15.) In such a model, the delay in time for the animal, typically a rat or mouse, to enter the chamber (the "latency period") is a measure of the animals' memory of the previous experience in receiving a foot shock. The longer is the latency period, the better is the memory enhancing effect of the test compound.

Using these animal models, it has been found that ACPC and 7KYN facilitate recall of a passive avoidance (i.e., an inhibitory avoidance) task in mice. These compounds also antagonize memory deficits in this task that are produced by pentylenetetrazol, a drug with known amnesic properties, and improve memory deficits induced by hypoxia.

Specifically, FIG. 1 shows the effect of pretraining administration of ACPC, 7KYN, DCS, 57DKYN, or FG7142 on passive avoidance acquisition-retention 24 hours after training in mice. The drugs were given prior to training, while testing occurred 24 hours after training. Administration of either ACPC, 7KYN, DCS, 57DKYN, or FG7142 resulted in significantly increased step-through latencies as compared to the control (saline) (SAL) group. Thus, compounds possessing functional antagonist properties at the NMDA receptor complex through a specific action at the associated strychnine-insensitive glycine site, like ACPC, 7KYN, and 5–7KYN, facilitate learning and memory of an inhibitory avoidance task. The facilitatory effect of these compounds was similar to that observed with D-cycloserine, a positive NMDA modulator at the strychnine-insensitive glycine site, and with FG7142, a benzodiazepine receptor inverse agonist.

Figure 2:
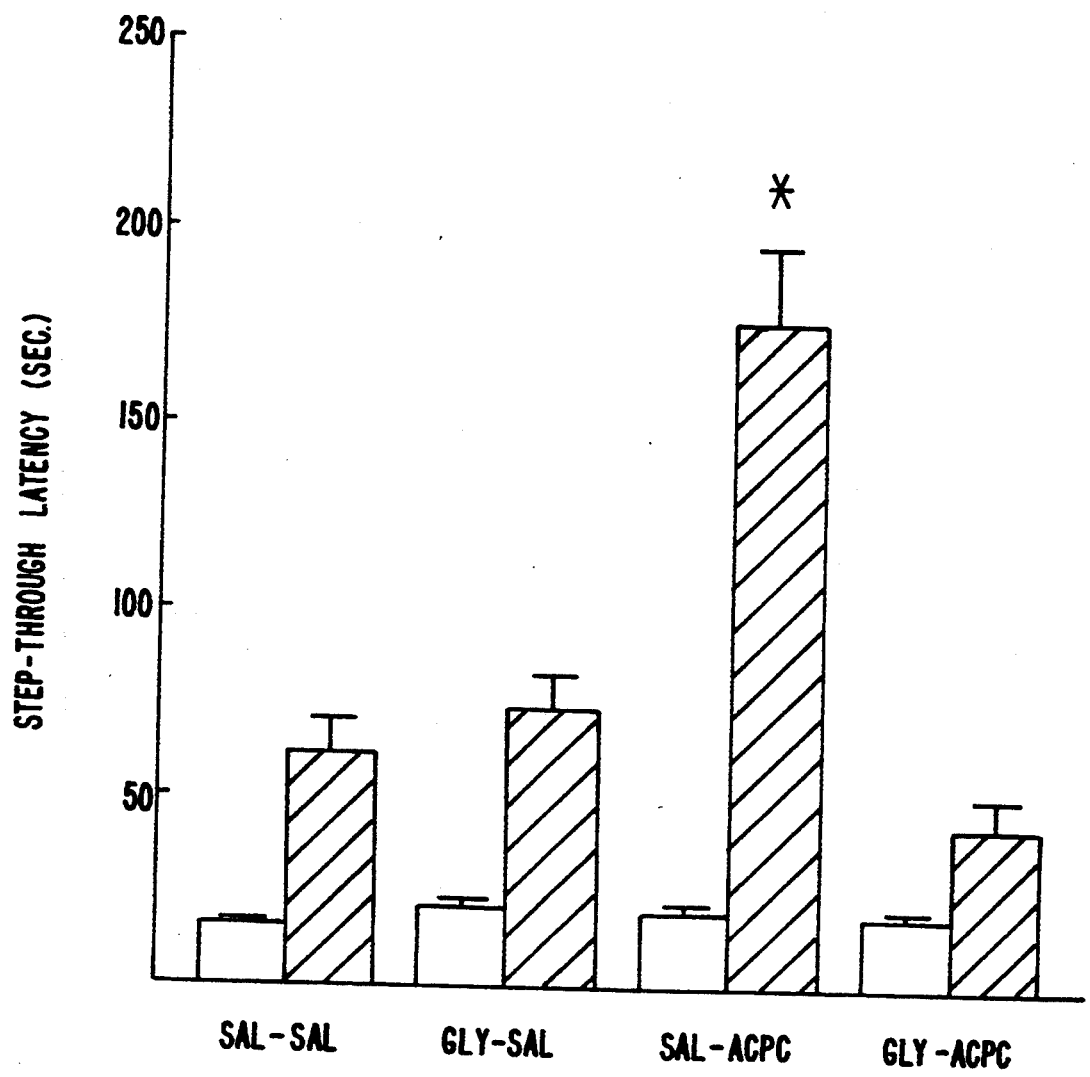
FIG. 2 is a graphical representation depicting the ability of glycine to antagonize 1-aminocyclopropanecarboxylic acid induced facilitation of acquisition-retention. Glycine (1 gram/kilogram (g/kg)) was administered 75 minutes before training and ACPC (400 milligrams/kilogram (mg/kg)) was administered 30 minutes before training. Training was performed with a 0.25 mA shock. Testing was 24 hours after training. Unfilled bars represent latency of non-shocked animals. Hatched bars represent latency 24 hours after training. The symbol "*" represents results that were significantly different from the control group ($p<0.05$ Mann-Whitney U-test). The ability of glycine to antagonize the effects of ACPC in this measure clearly demonstrates that ACPC acts as a functional antagonist through the strychnine-insensitive glycine receptor in the passive avoidance paradigm.

The antagonism by glycine of the 1-aminocyclopropanecarboxylic acid (ACPC) induced facilitation of acquisition-retention is shown in FIG. 2. Glycine (GLY, 1 gram/kilogram (g/kg)) was administered 75 minutes before training and ACPC (400 milligrams/kilogram (mg/kg)) was administered 30 minutes before training. Training was performed with a 0.25 mA shock. Testing was 24 hours after training. The ability of glycine to antagonize the facilitatory effects of ACPC in this measure clearly demonstrates that the cognitive enhancing properties of ACPC result from its action at the strychnine-insensitive glycine site as a functional NMDA receptor antagonist.

Figure 3:
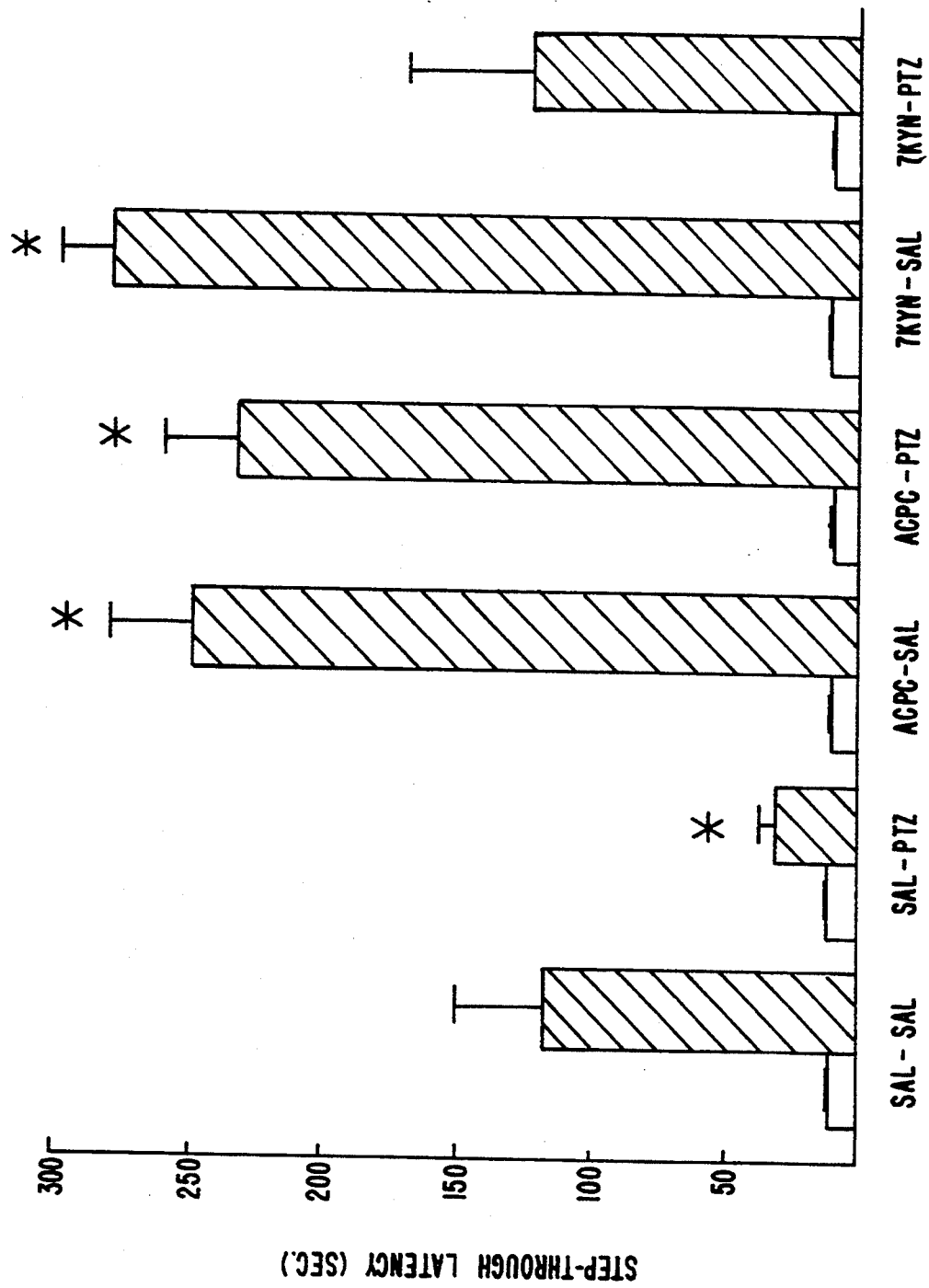
FIG. 3 is a graphical representation showing the effects of ACPC and 7-chlorokynurenic acid (7KYN) on the passive avoidance retention deficit induced by pentylenetetrazol (PTZ). ACPC (400 mg/kg) and 7KYN (30 mg/kg) were administered i.p. 30 minutes before training. A convulsant dose of PTZ (45 mg/kg), known to produce severe amnesia, was administered immediately after training. PTZ produced convulsions in all animals. Neither ACPC nor 7KYN antagonized PTZ induced seizures, but ACPC significantly reduced PTZ seizure latency. Training was performed with a 0.25 mA shock. Testing was 24 hours later. Unfilled bars represent latency of non-shocked animals. Hatched bars represent latency 24 hours after training. The symbol "*" represents results that were significantly different from the control group ($p<0.05$ Mann-Whitney U-test). These results show that, besides facilitating inhibitory avoidance acquisition-retention, ACPC and 7KYN protect against amnesia induced by PTZ. The protection afforded by ACPC was significantly better than that observed with 7KYN.

FIG. 3 is a graphical representation showing that ACPC and 7-chlorokynurenic acid (7KYN) protect against passive avoidance retention deficits induced by pentylenetetrazol (PTZ). ACPC (400 mg/kg) and 7KYN (30 mg/kg) were administered i.p. 30 minutes before training. A convulsant dose of PTZ (45 mg/kg), known to produce severe amnesia, was administered immediately after training. PTZ produced convulsions in all animals. Neither ACPC nor 7KYN antagonized PTZ induced seizures. These results show that, besides facilitating inhibitory avoidance acquisition-retention, ACPC and 7KYN protect against amnesia induced by PTZ. The protection afforded by ACPC was significantly better than that observed with 7KYN.

Figure 4:
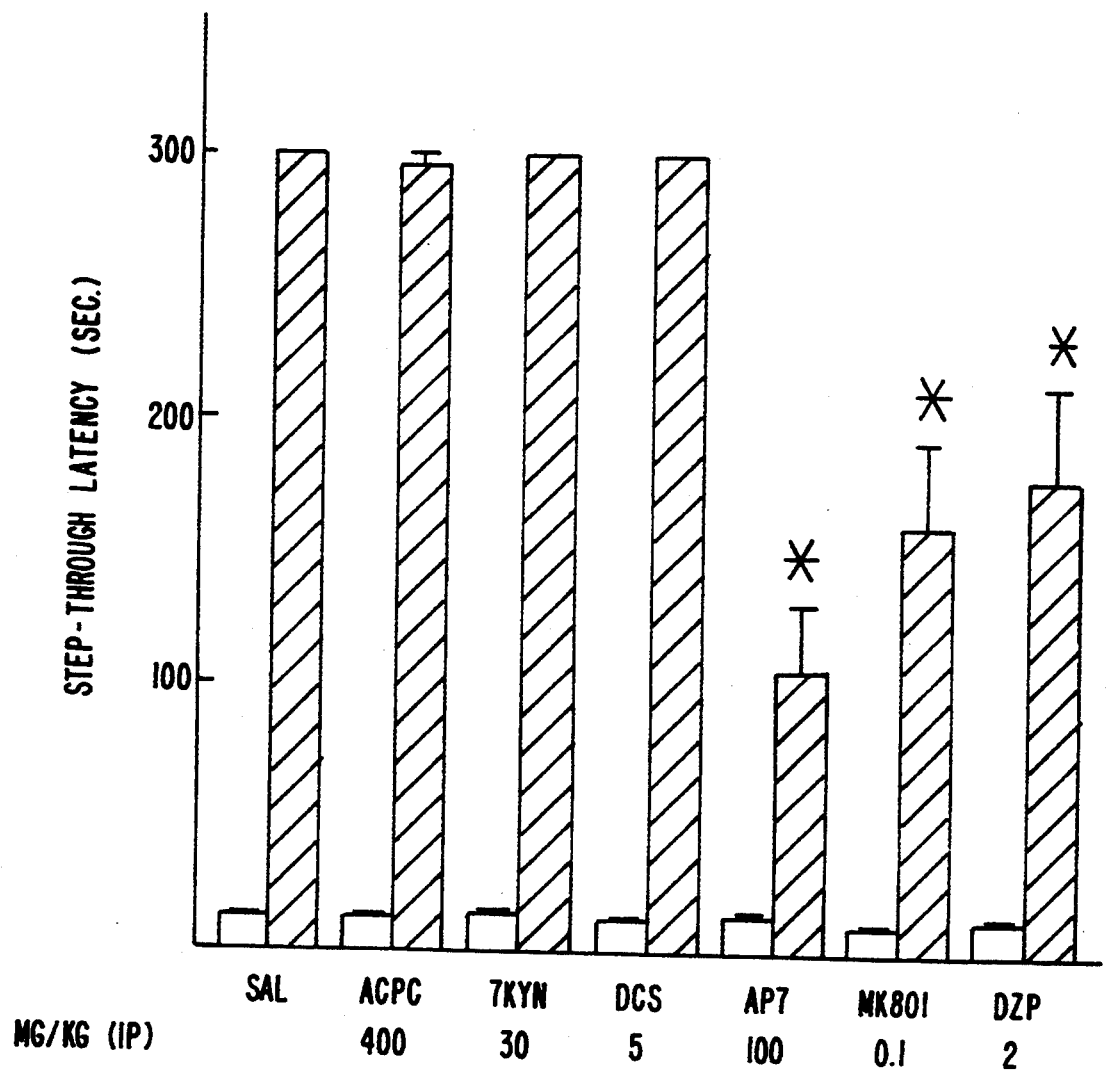
FIG. 4 is a graphical representation depicting the effects of NMDA receptor complex ligands and diazepam (DZP) on passive avoidance acquisition-retention. All drugs were administered i.p. 30 minutes before training. Training was performed with a 0.625 mA shock. Testing was 24 hours later. Unfilled bars represent latency of non-shocked animals. Hatched bars represent latency 24 hours after training. The symbol "*" represents results that were significantly different from the control group ($p<0.05$ Mann-Whitney U-test). These data demonstrate that in contrast to glycinergic compounds at the strychnine-insensitive receptor, other NMDA antagonists possess amnesic properties. Thus, the competitive NMDA antagonist AP-7 and the use dependent channel blocker, MK-801, interfere with passive avoidance acquisition-retention. A similar effect is observed with diazepam, a benzodiazepine with well-described amnesic properties.

The effects of NMDA receptor complex ligands and DZP on passive avoidance acquisition-retention are shown in FIG. 4. All drugs were administered i.p. 30 minutes before training. Administration of ACPC, 7KYN, and DCS gave results comparable to that of the control group. Administration of AP7, MK-801, or DZP resulted in significantly decreased step-through latencies when compared to the control group. These data demonstrate that the competitive NMDA antagonist AP-7 and the use dependent channel blocker, MK-801, interfere with passive avoidance acquisition-retention. A similar effect is observed with diazepam, a benzodiazepine with well-described amnesic properties. These data demonstrate that, in contrast to compounds binding at the strychnine-insensitive receptor, NMDA antagonists acting at other recognition sites of the NMDA receptor complex possess amnesic properties.

Figure 5:
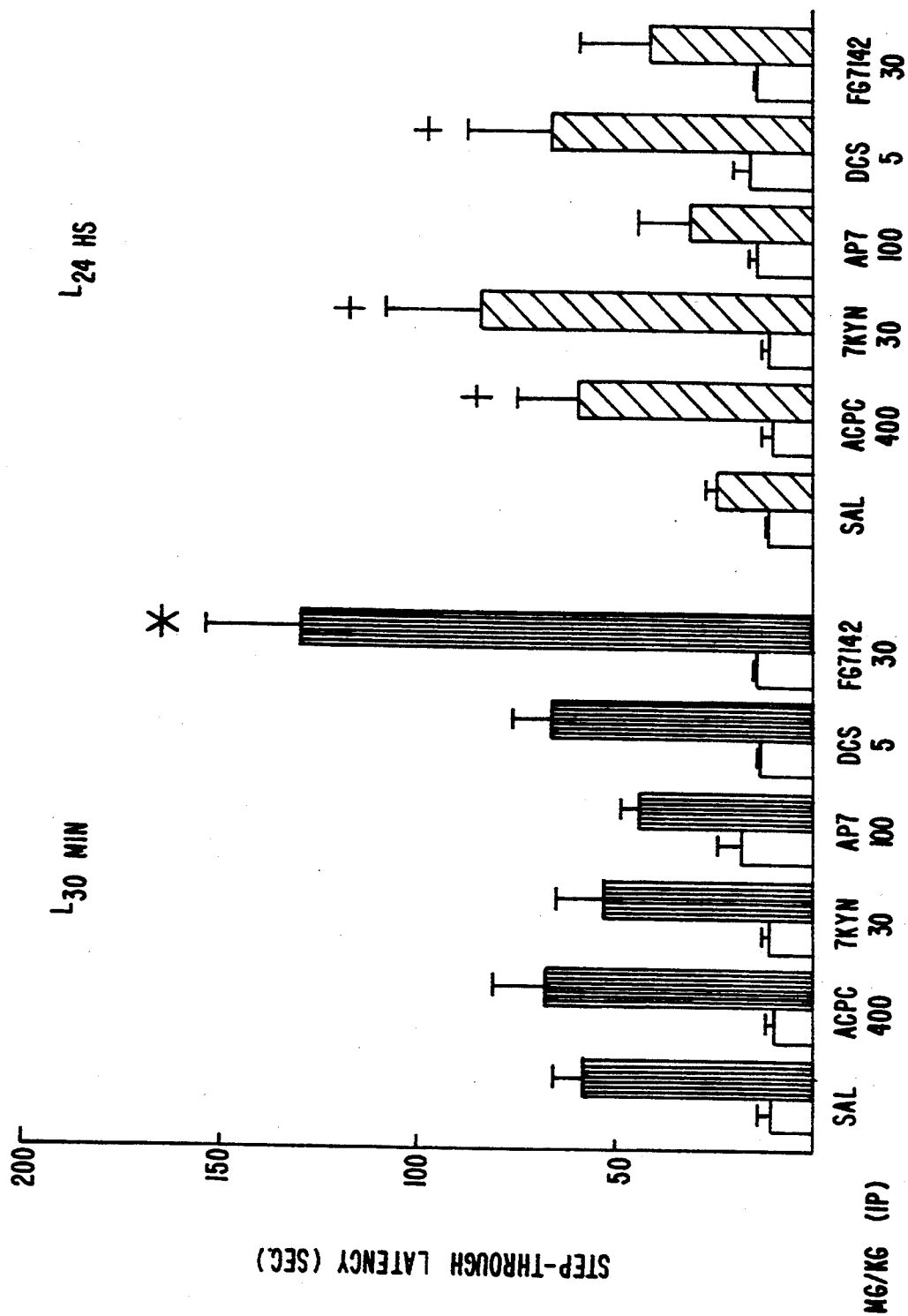
FIG. 5 is a graphical representation showing the effects of NMDA receptor complex ligands and FG7142 on retention of a passive avoidance task 30 minutes and 24 hours after training. All compounds were administered i.p. immediately after training. Training was with a 0.25 mA shock. Unfilled bars represent latency of non-shocked animals. Solid bars represent latency 30 minutes after training. Hatched bars represent latency 24 hours after training. The symbols "*" and "+" represents results that were significantly different from the control group ($p<0.05$ Mann-Whitney U-test). These data show that functional NMDA antagonists at the strychnine-insensitive glycine site facilitate retention of an inhibitory avoidance task also when administered post-training.

FIG. 5 is a graphical representation showing the effects of NMDA receptor complex ligands and FG7142 on retention of a passive avoidance task 30 minutes and 24 hours after training. All compounds were administered i.p. immediately after training. FG7142 resulted in a statistically different step-through latency at 30 minutes when compared to the control group. Administration of ACPC, 7KYN, and DCS produced statistically significant differences in step through latencies 24 hours after training when compared to the control group. Thus, functional NMDA antagonists at the strychnine-insensitive glycine site facilitate retention of an inhibitory avoidance task also when administered post-training.

Figure 6:
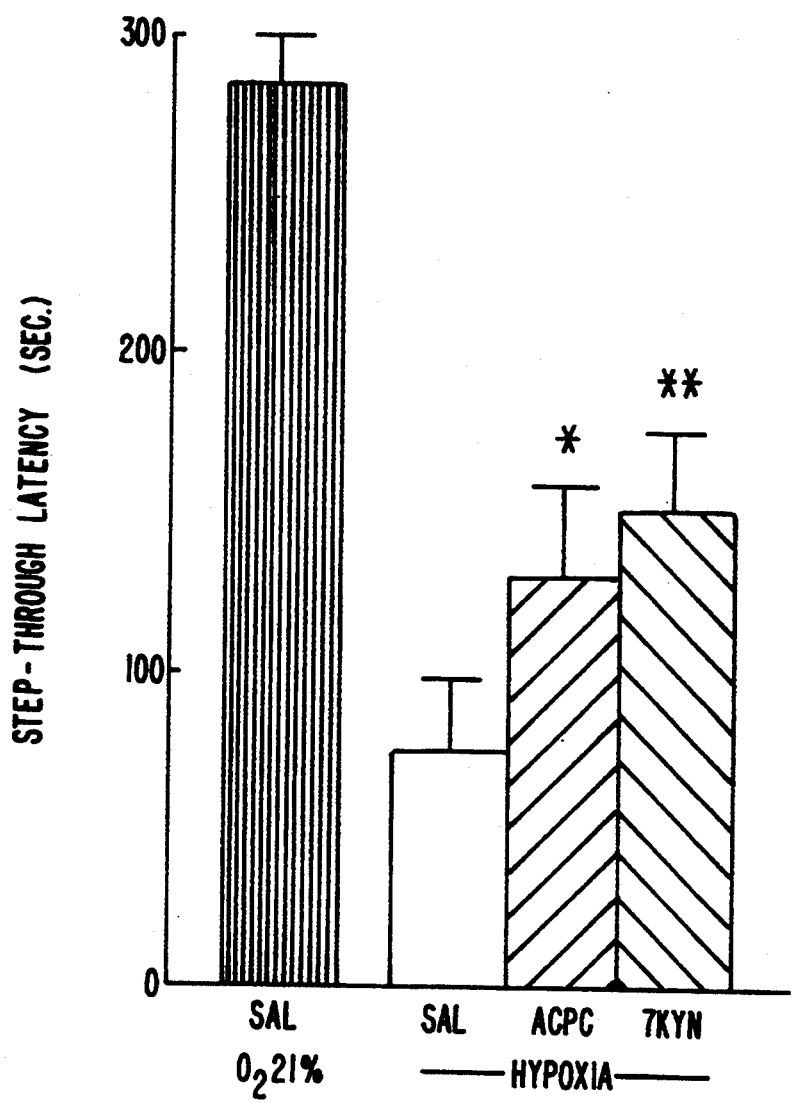
FIG. 6 is a graphical representation showing the effects of ACPC and 7KYN on the passive avoidance acquisition-retention deficit induced by hypoxia. ACPC (400 mg/kg) and 7KYN (30 mg/kg) were administered i.p. immediately before hypoxia. Hypoxia was induced by exposing the animals to a 7% oxygen environment for 30 minutes immediately before passive avoidance training. Training was performed with a 0.625 mA shock. Testing was 7 days later. The filled bar represents latency of animals that were not submitted to hypoxia. The unfilled bar represents latency of animals submitted to hypoxia with saline pretreatment. Hatched bars represent latency of animals submitted to hypoxia but receiving pre-treatment with ACPC (400 mg/kg) or 7KYN (30 mg/kg). The symbols "*" and "**" represents results that were significantly different from the SAL-hypoxia group ($p<0.05$ and $p<0.01$, respectively, Mann-Whitney U-test). These results show that ACPC and 7KYN significantly protect against amnesia induced by hypoxia.

The effects of functional NMDA receptor antagonists on inhibitory avoidance acquisition-retention deficits induced by hypoxia are shown in FIG. 6. All drugs were administered i.p. immediately before hypoxia. Hypoxia was induced by exposing the animals to a 7% oxygen environment for 30 minutes immediately before passive avoidance training. Animals were tested 7 days later. These results show that hypoxia induced acquisition-retention deficits of inhibitory avoidance can be significantly antagonized by ACPC and 7KYN.

The disclosures in this application of all articles and references, including patent documents, are incorporated herein by reference.

It is to be understood that the above description is intended to be illustrative and not restrictive. Many embodiments will be apparent to those of skill in the art upon reviewing the above description. The scope of the invention should, therefore, be determined not with reference to the above description, but should instead be determined with reference to the appended claims, along with the full scope of equivalents to which such claims are entitled.

The invention has been described above in some detail for the purposes of clarity and understanding. It will be apparent, however, that certain changes and modifications can be practiced within the scope of the appended claims.

What is claimed is:

1. A method to treat a cognitive deficit consequent to a neurological disorder resulting from or associated with chronic neuronal degeneration or an acute brain injury, comprising administering to a patient suffering from a cognitive deficit resulting from hypoxia, Parkinson disease, dementia, lathyrism, neurodegenerative diseases or head trauma a therapeutically-effective amount of at least one compound having the formula:

wherein:
A is -$CO_2H$ or a pharmaceutically acceptable ester, amide, or salt thereof; and
X is -$NR^1R^2$ or a pharmaceutically acceptable acid addition salt thereof, wherein $R^1$ and $R^2$ are selected independently from the group consisting of hydrogen and lower alkyl substituted optionally from the group consisting of halogen, hydroxyl, alkoxy, oxo, mercapto, aryl or amino,
to thereby improve or enhance the memory of said patient.

2. The method of claim 1, wherein said at least one compound is 1-aminocyclopropanecarboxylic acid.

* * * * *